(12) United States Patent
Huynh

(10) Patent No.: US 9,795,702 B2
(45) Date of Patent: Oct. 24, 2017

(54) APPARATUS AND METHOD FOR DIFFUSING A CHEMICAL SUBSTANCE

(71) Applicant: DC & BV France Holding SAS, Paris (FR)

(72) Inventor: Valery Huynh, Chelles (FR)

(73) Assignee: DC & BV France Holding SAS (FR)

( * ) Notice: Subject to any disclaimer, the term of this patent is extended or adjusted under 35 U.S.C. 154(b) by 109 days.

(21) Appl. No.: 14/894,904

(22) PCT Filed: Jan. 13, 2015

(86) PCT No.: PCT/EP2015/050474
§ 371 (c)(1),
(2) Date: Nov. 30, 2015

(87) PCT Pub. No.: WO2015/107036
PCT Pub. Date: Jul. 23, 2015

(65) Prior Publication Data
US 2016/0114069 A1  Apr. 28, 2016

(30) Foreign Application Priority Data

Jan. 15, 2014 (EP) .................................... 14151226
Nov. 20, 2014 (EP) .................................... 14194082

(51) Int. Cl.
*A61L 9/00* (2006.01)
*B01F 3/04* (2006.01)
(Continued)

(52) U.S. Cl.
CPC ........... *A61L 9/032* (2013.01); *A01M 1/2072* (2013.01); *A01M 1/2077* (2013.01);
(Continued)

(58) Field of Classification Search
CPC ........ B01F 3/04; B01F 3/04007; A61L 9/032; A61L 9/037; A61L 9/015; A61L 9/00; A61L 9/02
(Continued)

(56) References Cited

U.S. PATENT DOCUMENTS 4,968,456 A * 11/1990 Muderlak ............... A61L 9/122
137/60
6,104,866 A   8/2000 DeWitt et al.
(Continued)

FOREIGN PATENT DOCUMENTS

| EP | 1637169 A1 | 3/2006 |
| WO | 2005092400 A1 | 10/2005 |
| WO | 2011028259 A2 | 3/2011 |

OTHER PUBLICATIONS

International Search Report and Written Opinion for Application No. PCT/EP2015/050474 dated Jul. 22, 2015.

*Primary Examiner* — Robert A Hopkins
(74) *Attorney, Agent, or Firm* — Lerner, David, Littenberg, Krumholz & Mentlik, LLP

(57) ABSTRACT

The present invention provides an apparatus for diffusing a chemical substance comprising: a chamber having a diffusing member arranged to diffuse a chemical substance to air disposed within the chamber, wherein the chamber is in communication with an air-inlet arranged to receive air from an exterior of the chamber and an air-outlet arranged to expel air from within the chamber.

14 Claims, 13 Drawing Sheets

(51) Int. Cl.
- A61L 9/03 (2006.01)
- A01M 1/20 (2006.01)
- F23D 3/40 (2006.01)

(52) U.S. Cl.
CPC ........... *A01M 1/2088* (2013.01); *A61L 9/037* (2013.01); *B01F 3/04007* (2013.01); *F23D 3/40* (2013.01); *A61L 2209/133* (2013.01); *A61L 2209/134* (2013.01); *A61L 2209/135* (2013.01); *F23D 2900/03081* (2013.01)

(58) Field of Classification Search
USPC ............ 261/26, 30, 78.2, 115, 116, DIG. 88, 261/DIG. 89; 422/124
See application file for complete search history.

(56) References Cited

U.S. PATENT DOCUMENTS

| | | | |
|---|---|---|---|
| 8,147,097 B1 | 4/2012 | Hsiao | |
| 8,517,351 B2* | 8/2013 | Sharma | A01M 1/2033 239/44 |
| 2008/0226269 A1 | 9/2008 | DeWitt et al. | |
| 2010/0059601 A1* | 3/2010 | Bankers | A01M 1/2077 239/44 |

* cited by examiner

APPARATUS AND METHOD FOR DIFFUSING A CHEMICAL SUBSTANCE

CROSS-REFERENCE TO RELATED APPLICATIONS

The present application is a national phase entry under 35 U.S.C. §371 of International Application No. PCT/EP2015/050474 filed Jan. 13, 2015 published in English, which claims priority from EP Application No. 14151226.9 filed Jan. 15, 2014 and EP Application No. 14194082.5 filed Nov. 20, 2014, all of which are incorporated herein by reference.

TECHNICAL FIELD

This particular invention relates to an apparatus and method for diffusing a chemical substance, and particularly, although not exclusively, to an apparatus arranged to diffuse a scent substance to a defined area space.

BACKGROUND

Various people including business owners, environmental specialists, building designers and event organisers recognize the need to control the quality of air within a defined space. Often, by controlling the air quality, the habitability of the space is improved and may assist in improving the quality of the time a person may spend in that space. Such an improvement has been used for example in homes, schools and various businesses so as to enhance the attractiveness of the space.

One example method of controlling the air quality of a space is to diffuse a compound to an area space. Sometimes, this compound may be a scented compound as an aromatherapy compound which offers an attractive and therapeutic scent to the surrounding environment. By diffusing a scent into an area, business owners and event organisers are able to improve the attractiveness and comfort of a particular area. As an example, retail outlets may provide a scent to a particular retail space which matches with their desired image so as to increase the pleasantness for its shoppers, whilst hotel owners may also use scents so as to improve the hospitability and pleasantness of a space for its patrons.

Whilst there are methods to distribute scented substances into the air, the distribution of the scent is often limited to small and confined spaces, such as toilets, kitchens, living rooms or small pockets of space. For larger pockets of space which may have its own air-conditioning systems or may be subjected to higher user traffic or regular exposure to external elements, such as hotel lobbies, concert halls or train stations, these small scale scent distribution methods do not operate effectively and thus reduce the effectiveness of any improvement in air quality.

SUMMARY OF THE INVENTION

In accordance with a first aspect of the present invention, there is provided an apparatus for diffusing a chemical substance comprising: a chamber having a diffusing member arranged to diffuse a chemical substance to air disposed within the chamber, wherein the chamber is in communication with an air-inlet arranged to receive air from an exterior of the chamber and an air-outlet arranged to expel air from within the chamber.

In an embodiment of the first aspect, the air inlet and the air outlet is positioned such that the air flowing from the air inlet and out the air outlet is substantially passed through the diffusing member of the chamber.

In an embodiment of the first aspect, the chamber is defined by a housing arranged to surround the diffusing member.

In an embodiment of the first aspect, the air-outlet is arranged to expel air at an angle relative to an axis of the base.

In an embodiment of the first aspect, the angle is an acute angle.

In an embodiment of the first aspect, the apparatus further comprises a fan arranged to drive air from the air-inlet and through the chamber to be expelled through the air-outlet.

In an embodiment of the first aspect, the diffusing member is in liquid communication with a container arranged to contain the chemical substance.

In an embodiment of the first aspect, the liquid communication between the diffusing member and the container is formed by a wick.

In an embodiment of the first aspect, the diffusing member is heated.

In an embodiment of the first aspect, the diffusing member is heated to a temperature between 50 to 80 degrees Celsius.

In an embodiment of the first aspect, the container includes a conduit extending from the container to an opening disposed on the housing.

In an embodiment of the first aspect, the opening disposed on the housing includes a plug pivotably connected to the housing such that the plug is arranged to be pivotably inserted into the conduit to seal the container.

In an embodiment of the first aspect, the fan is controlled by a controller to vary the speed of the fan.

In an embodiment of the first aspect, the chemical substance is an aromatherapy compound.

In accordance with a second aspect of the present invention, there is provided a method of diffusing a scent to an area space by use of an apparatus in accordance with any one of the embodiments of the first aspect.

In accordance with a third aspect of the present invention, there is provided an apparatus for diffusing a chemical substance comprising: a chamber having a diffusing member arranged to diffuse a chemical substance to air disposed within the chamber, wherein the chamber is in communication with an air-inlet arranged to receive air from an exterior of the chamber and an air-outlet arranged to expel air from within the chamber.

In accordance with an embodiment of the third aspect, the chamber is defined by a housing arranged to surround the diffusing member.

In accordance with an embodiment of the third aspect, the apparatus further comprises a fan arranged to drive air from the air-inlet and through the chamber to be expelled through the air-outlet.

In accordance with an embodiment of the third aspect, the diffusing member is in liquid communication with a container arranged to contain the chemical substance.

In accordance with an embodiment of the third aspect, the apparatus further includes a power conduit arranged to deliver electrical power to the apparatus from a power source, wherein the power conduit is rotatable relative to the housing.

In accordance with an embodiment of the third aspect, the power conduit includes a removable electrical plug member arranged to be connected to the power source.

In accordance with an embodiment of the third aspect, the power conduit includes a rotatable circuit member arranged to form a continuous electrical connection between the power conduit and the apparatus as the power conduit is rotated relative to the housing.

In accordance with an embodiment of the third aspect, the rotatable circuit member is a printed circuit board having a circular conductive track arranged to form the continuous electrical connection between the power conduit and the apparatus as the power conduit is rotated relative to the housing.

In accordance with an embodiment of the third aspect, the diffusing member is a catalytic burner having a ceramic matrix, the ceramic matrix arranged to be heated by an electric heating element.

In accordance with an embodiment of the third aspect, the catalytic burner is heated to a temperature of between 50 to 80 degrees Celsius.

In accordance with an embodiment of the third aspect, the power conduit includes a detent arranged to restrict the rotation of the power conduit about the housing.

In accordance with an embodiment of the third aspect, the power source is a mains power supply socket.

In accordance with an embodiment of the third aspect, the fan is controlled by a controller to vary the speed of the fan.

In accordance with an embodiment of the third aspect, the chemical substance is an aromatherapy compound.

In accordance with an embodiment of the third aspect, the container is arranged to slidably engage or disengage with the housing.

BRIEF DESCRIPTION OF THE DRAWINGS

Embodiments of the present invention will now be described, by way of example, with reference to the accompanying drawings in which.

DETAILED DESCRIPTION OF THE PREFERRED EMBODIMENT

Figure 1:
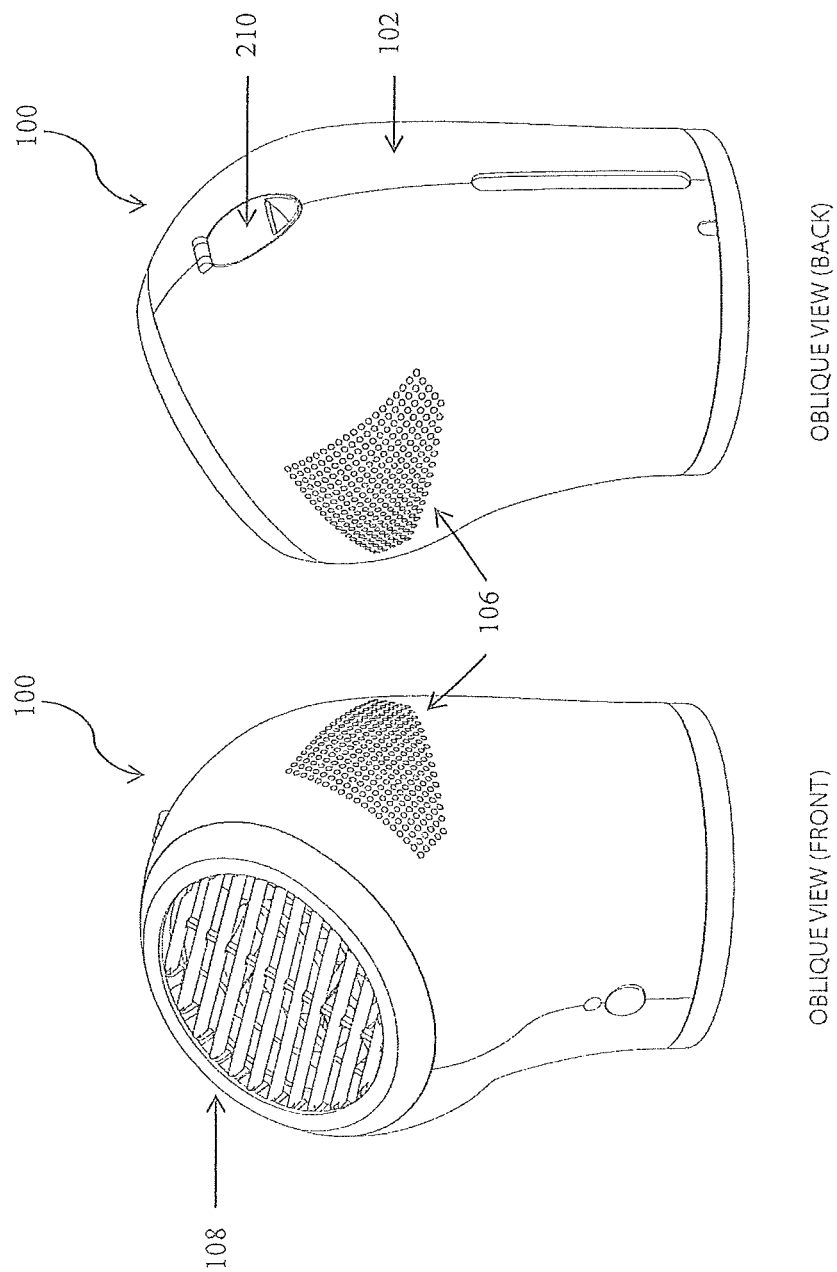
FIG. 1 is a front and rear perspective view of an apparatus for diffusing a chemical substance in accordance with one embodiment of the present invention.
Figure 2:
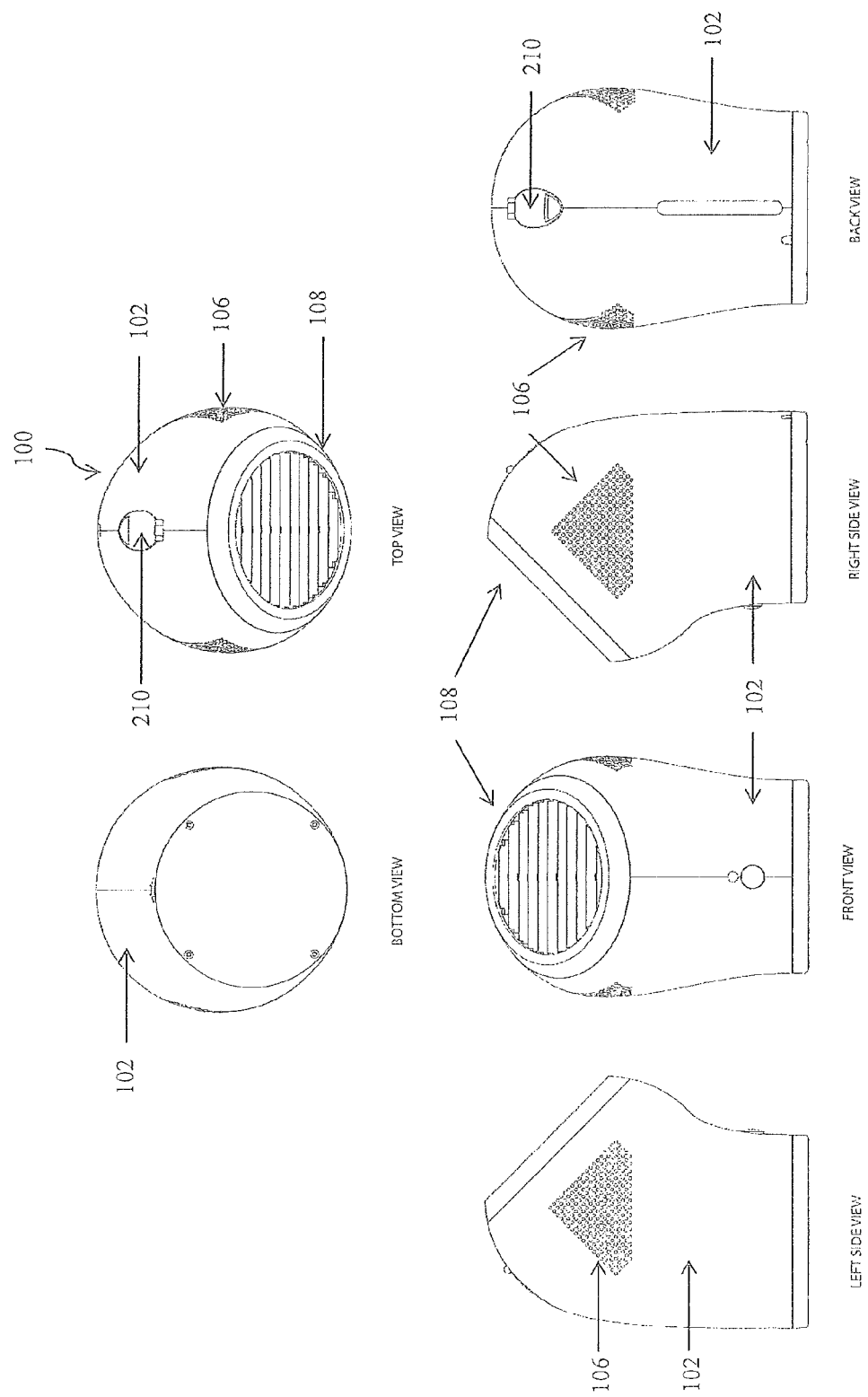
FIG. 2 is a top, side, front and rear view of the apparatus of FIG. 1.

With reference to FIGS. 1 and 2, there is illustrated an embodiment of an apparatus for diffusing a chemical substance comprising: a chamber having a diffusing member arranged to diffuse a chemical substance to air disposed within the chamber, wherein the chamber is in communication with an air-inlet arranged to receive air from an exterior of the chamber and an air-outlet arranged to expel air from within the chamber.

In this embodiment, the apparatus for diffusing a chemical substance 100 includes a housing 102 arranged to house within a chamber 104 which has an air-inlet portion 106 and an air-outlet portion 108. The apparatus is arranged to be placed on its base 110 so that it can be supported on a floor, shelf or any other surface so that in operation, the apparatus is arranged to diffuse a chemical substance to the surrounding space.

In operation, the apparatus 100 can be placed on a surface, such as a table, floor or shelf of a space and allow to run continuously to diffuse a chemical substances stored within the apparatus 100. In operation, the apparatus 100 has an operating fan 202 within the housing 102 which drives air from the surrounding space into the chamber 104 of the apparatus 100 through the air-inlet vents 106. Air which travels through the air-inlet vents 106 are then passed through a diffusing member 204 within the chamber 104 which in turns diffuses the chemical substance stored within the apparatus to the air within the chamber 104. This air, which is stored within the chamber 104 is in turn mixed with the diffused chemical substance and then expelled from the chamber 104 via the air-outlet vent 108. Resultant from the operation of the apparatus 100 is that the chemical substance stored within the apparatus 100 is then diffuse to the surrounding air of the apparatus 100.

Figure 5:
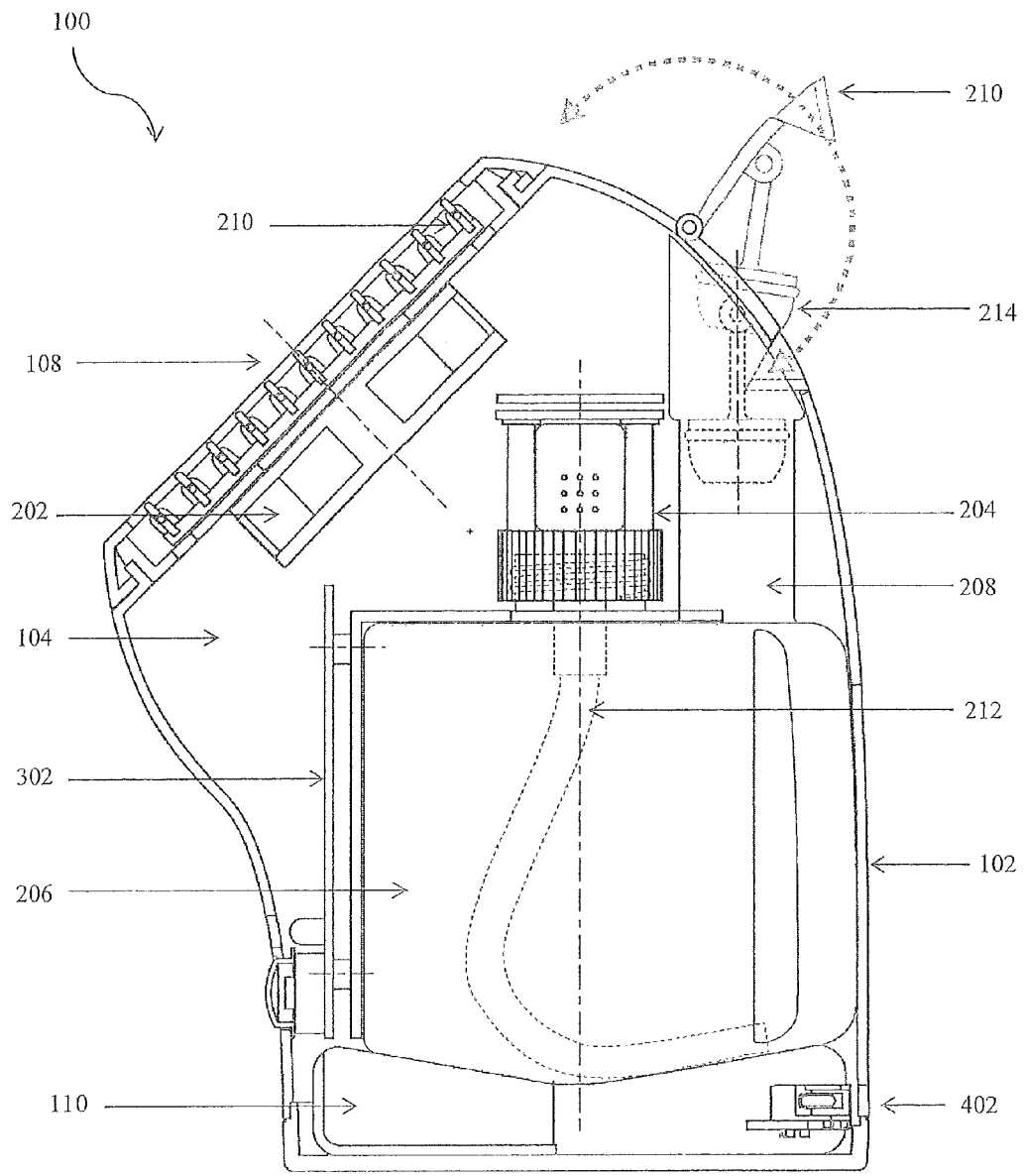
FIG. 5 is a cut away side view of the apparatus of FIG. 1.
Figure 6:
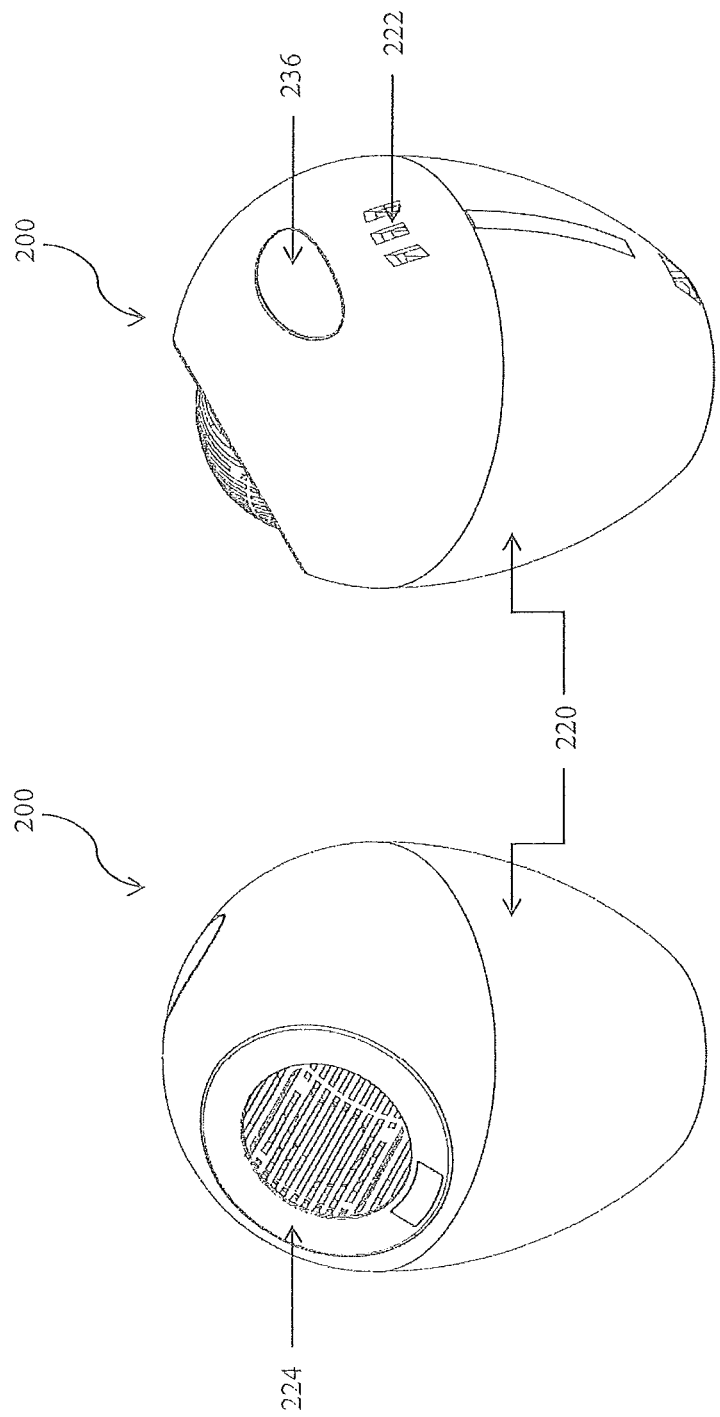
FIG. 6 is a front and rear perspective view of an apparatus for diffusing a chemical substance in accordance with another embodiment of the present invention.
Figure 7:
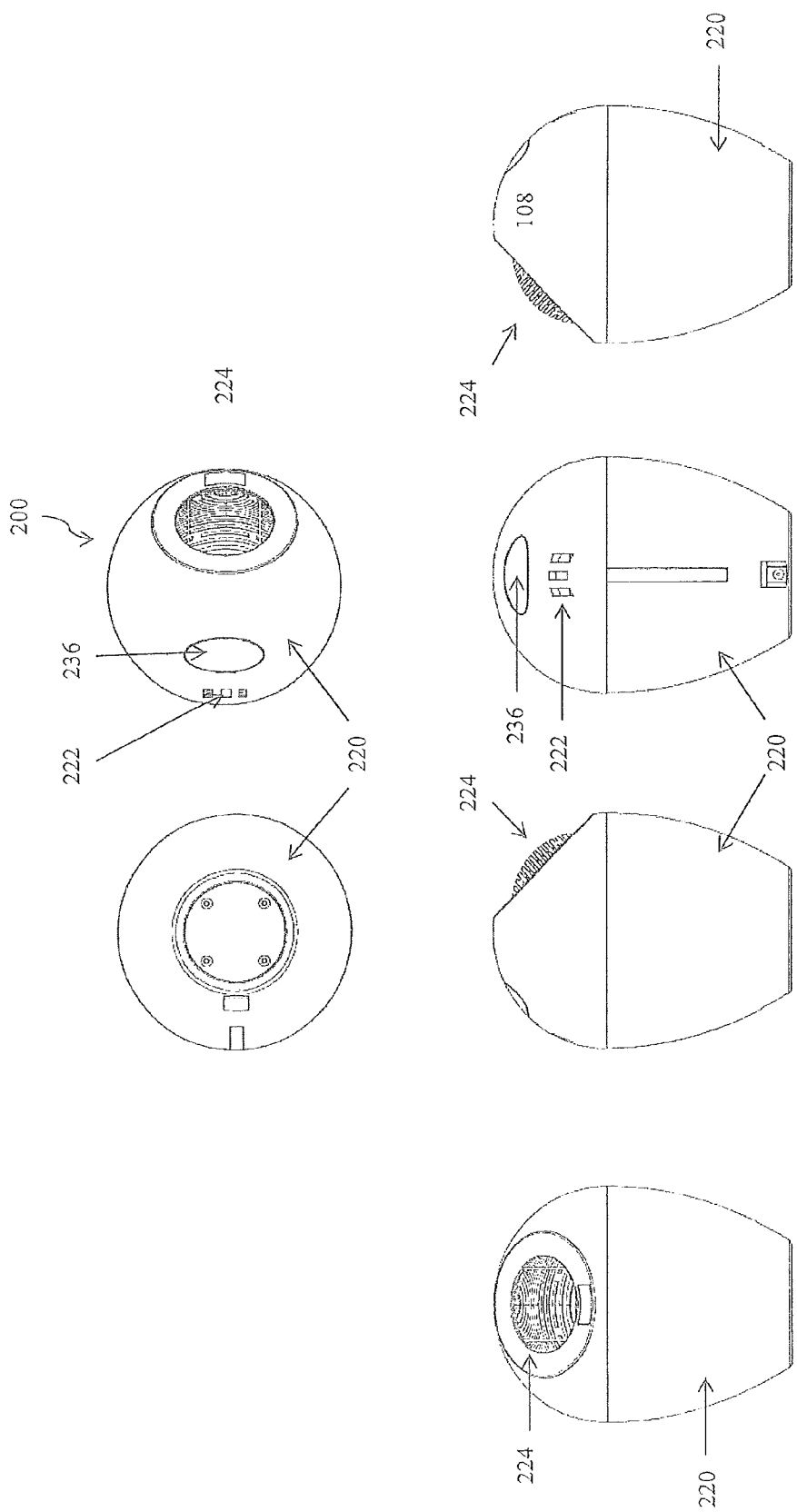
FIG. 7 is a top, side, front and rear view of the apparatus of FIG. 6.

Preferably, as shown in FIGS. 1 and 2, the air-outlet 108 is placed at an angle from the base such that air expelled from the chamber 104 within the housing 102 can be directed in a sideways and upwards direction (this is more clearly shown in the side profile of FIGS. 2 and 5). This embodiment is advantageous in that scented air which exits the air-outlet 108 of the apparatus 100 can be distributed away from the apparatus 100 in a generally upwards direction so as to maximize the mixture of the surrounding atmosphere with the scented air or air with the diffused chemical substance being distributed by the apparatus 100.

In one example embodiment, the chemical substance which is diffused by the apparatus 100 may be water, a medical compound, a disinfectant, a scented compound such as those used in aromatherapy or a perfumed compound or any other chemical substance. In these examples where the chemical substance includes a scented compound or perfumed substance, the apparatus 100 would effectively operate as a diffuser of these scented compounds to the surrounding space and provide a scent to the surrounding space.

Figure 3:
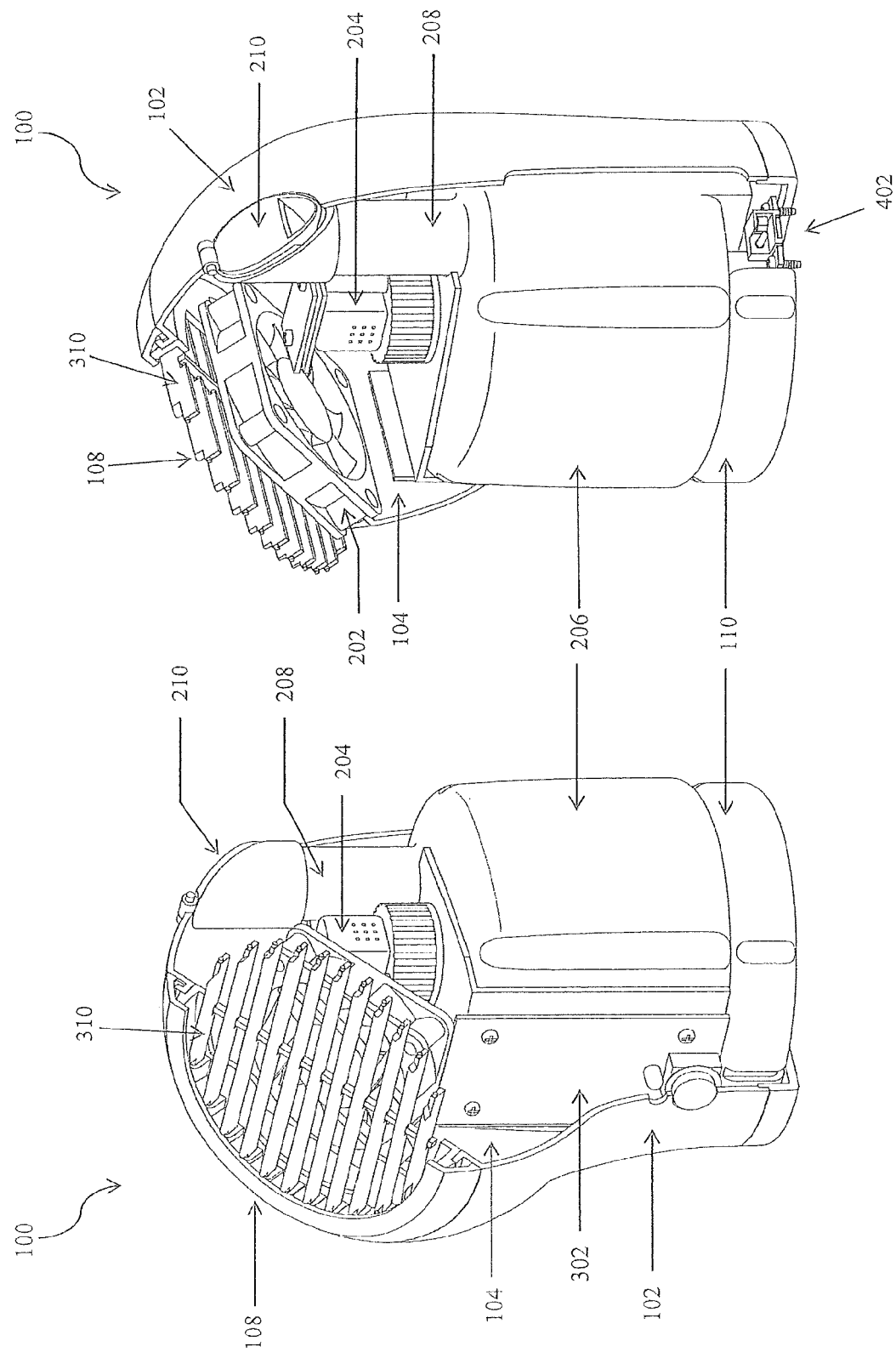
FIG. 3 is a front and rear cut away view of the apparatus of FIG. 1.
Figure 4:
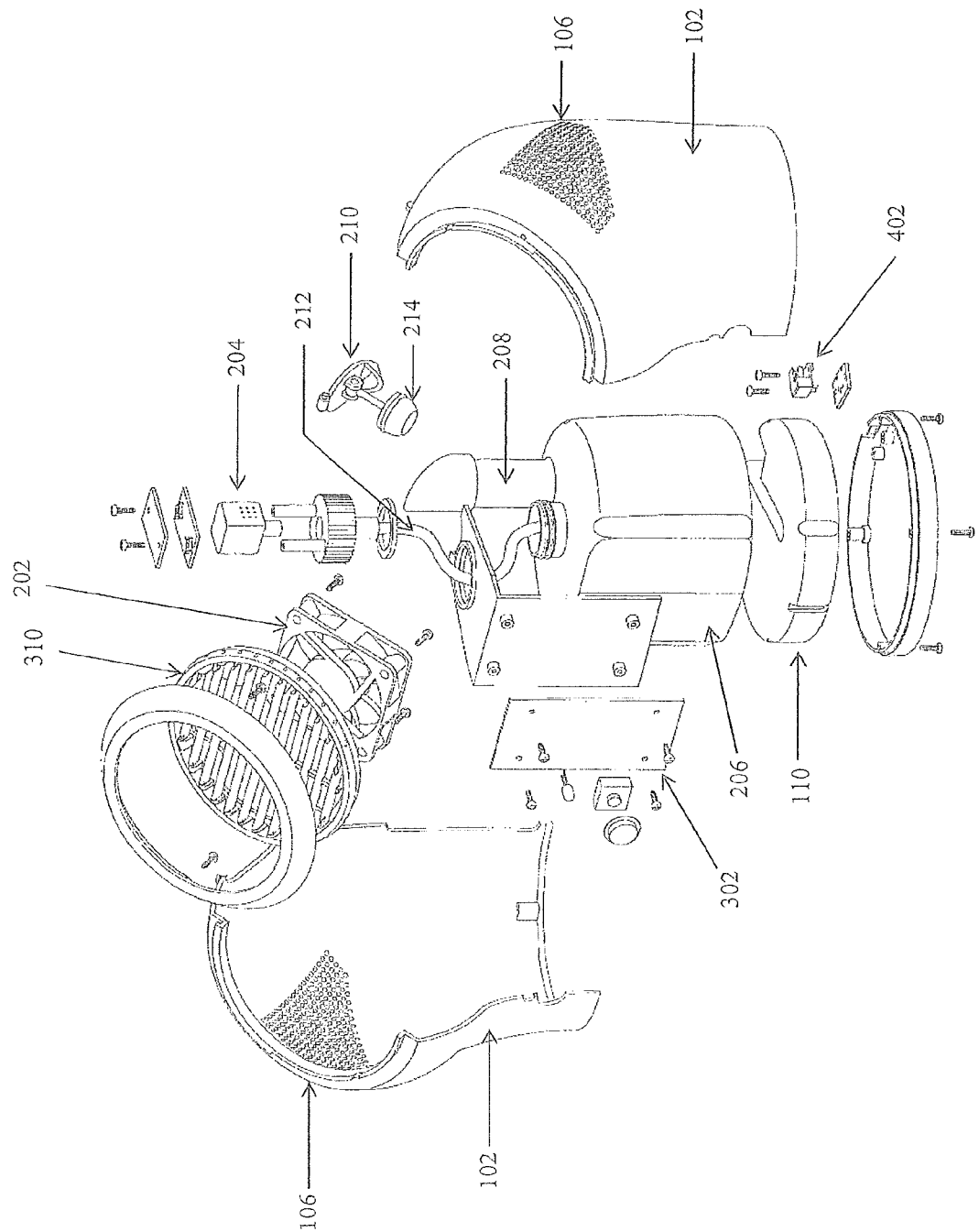
FIG. 4 is an exploded view of the apparatus of FIG. 1.

With reference to FIGS. 3 and 4, there is illustrated the internal components of the apparatus 100 in accordance with one embodiment of the present invention. As shown, the chamber 104 within the housing 102 of the apparatus is positioned between the air-inlet 106 and the air-outlet of the apparatus 108 so that air driven by the fan 202 can flow from the air-inlet 106, through the chamber 104 and exit via the air-outlet 108.

In this embodiment, the chamber 104 has a diffusing member 204, preferably disposed in the path of air flowing through the chamber 104 so that a substantial portion of the air passing through the chamber 104 can pass near or adjacent to the diffusing member 204. This in turn is advantageous in that the diffusing member 204 can increase the distribution of the chemical substance diffused by the diffusing member 204 to the air within the chamber 104.

As shown in these illustrations, the diffusing member. 204 is in liquid communication with a container 206 which is arranged to store the chemical substance diffused by the apparatus 100. In one example, in order to deliver the chemical substance stored within the container 206 to the diffusing member 204, a wick 212 made from cotton or polyester or any other suitable materials may be used to deliver the chemical substance to the diffusing member 204 via capillary action. In other example, a mechanical or electrical pump may be used to deliver the chemical substance.

Once the chemical substance is delivered to the diffusing member 204, the diffusing member 204 is arranged to diffuse the chemical substance to the air within the chamber 104. Preferably, the diffusing member 204 is made from a stone or ceramic material having a number of apertures which act as pores to increase the surface area of the diffusing member 204 so that more chemical substance can be exposed to the air surrounding the diffusing member 204. The diffusing member 204 may also be heated via a heat source, such as by an electric heater disposed in, on or adjacent to the diffusing member 204. By heating the diffusing member, the chemical substance delivered to the diffusing member 204 can be evaporated more quickly into the air within the chamber 104, and thus increasing the diffusion of the chemical substance.

Preferably, the temperature of the diffusing member 204 may also be controlled by a controller circuit which may be implemented in the form of an electronic logic circuit disposed on a print circuit board (PCB) 302. The controller circuit may provide an actuating function to the apparatus 100 as well as to control the heater of diffusing member 204 so as to control the temperature of the diffusing member 204. In some examples, the diffusing member 204 may also be heated to a temperature within a range of 50 to 90 degree Celsius. Experiments of heating the diffusing member 204 to this temperature have shown that there is an effective diffusion of certain types of chemical substances. Additionally, by heating the diffusing member 204 to this temperature range, pathogens in the air or in the chemical substances may be effectively destroyed. Thus the apparatus 100 may also provide a disinfectant function. This is particularly the case where the chemical compound diffused by the apparatus 100 contains an antiseptic substance such as an alcohol compound.

In this particular embodiment, a fan 202 is disposed adjacent to the air-outlet 108 so as to propel air through the chamber 104 of the apparatus 100. As a person skilled in the art would appreciate, the fan 202 can be disposed elsewhere on the apparatus 100. However, by placing the fan 202 adjacent to the air-outlet 108, the fan 202 may be easily removed through the air-outlet 108 for cleaning or maintenances. In these embodiments, the fan 202 may be removably connected to a power source or to the controller such that the entire air outlet 108 and fan 202 can be removed from the apparatus 100 for cleaning or maintenance. As shown in this example embodiment, the fan 202 is connected to a louver member 310 having a plurality of adjustable slats such that the direction of air flow is also adjustable. In other examples, the louver member 310 is rotatable and thus allowing for the air flow to be adjusted in any direction away from the air-outlet 108.

The apparatus 100, in some advanced embodiments, may also include a plurality of sensors and control logic implemented on the controller 302 so as to provide additional functionality to the apparatus 100. The controller board 302, apart from controlling the temperature of the diffusing member 204, may also control the fan 202 speed of the apparatus 100 so as to facilitate the necessary air flow to diffuse the chemical substance. In other examples, sensors within the chamber 104 can be connected to the controller 302 so as to detect the level of diffusion of the chemical components within the chamber 104 to match a predetermined or desirable level of diffusion, whilst the container 206 carrying the chemical substance may also include a sensor so as to detect the level of chemical substance remaining within the container 206. In another example, a sensor exterior to the apparatus 100 or disposed on the exterior of the housing 102 may detect the level of chemical substance in the surrounding air and in turn communicate this information to the controller 302 so as to increase or decrease the level of diffusion of the chemical substance.

In further advanced embodiments, the apparatus may include a network or communication port which can allow more than one apparatus to communicate with each other, or with a central controller or server so as to operate as a cluster or network to diffuse a scent to a specific area. Examples of such an operation may be large size areas such as hotel lobbies where various apparatuses 100 may be placed within the lobby of a hotel or large space and can be controlled individually or centrally to ensure a proper diffusion of the chemical substance during operation.

As shown in FIGS. 3 and 4, the container 206 which operates as a container or tank for the chemical substances may include a conduit 208 arranged to extend to an opening 210 on the housing 102. This is advantageous in that the housing 102 does not need to be removed to access the container 206 and thus minimizes the amount of time or effort required to refill the container 206. As shown in FIG. 5, the conduit 208 is sealed by a piston shaped plug 214 which is inserted into the conduit 108 to seal the container 206. The piston shaped plug 214 is also pivotally connected to the opening 210 such that when the opening 210 is pivoted upwardly, the piston shaped plug 214 is lifted from the conduit 208 so as to allow access to the container 206. For sealing the container 206, the piston shaped plug 214 is inserted into the conduit 208 and pushed down into the conduit 208 by a pivotal action of the opening 210.

Preferably, the apparatus 100 also includes a weighted base 110 made of a heavier material such as metal, stone or ceramic disposed below the container 206. The base 110 provides stability to the apparatus 100 and minimizes the chances of apparatus 100 from being tipped over when the container 206 is close to empty. As shown in this example, the air-outlet 108 is also disposed at an angle from the base 110, that is, at an angle from a vertical axis extending from the base 110. Preferably the angle is at approximately 45 degrees from the base 110, and thus the air within the chamber 104 can be expelled at a generally sideways and upwards profile yet the weighted base 110 assist in stabilising the apparatus 100 on a surface during operation.

In this example embodiment, the apparatus 100 is powered by an external power source which is connected to a power port 402 disposed adjacent to the base 110 of the apparatus 100. As the person skilled in the art would appreciate, the power port 402 can be disposed anywhere else on the apparatus 100. In some other example embodiments, the apparatus 100 may also be powered internally, such as by a battery or a rechargeable battery disposed adjacent to the base 110, or indeed, to replace the weighted base 110 itself. In other embodiments, a solar panel may also be included on the housing 102 so as to provide electrical power to operate part or all of the components of the apparatus 100.

Embodiments of the apparatus 100 may be advantageous in that the apparatus 100 may be used to diffuse chemical substances in a more effective manner, particularly in large spaces such as halls or lobbies. By using a controlled heated diffusing member and a fan member as well as the position of the diffusing member being disposed near or adjacent to the air flow between the air-inlet and the air-outlet, the diffusion of the chemical substances such as aromatherapy compounds can be completed much more effectively. Furthermore, the heated diffusion member also assists in destroying pathogens which are in the air and thus the apparatus also provides a cleaning or disinfecting affect, thus increasing the pleasantness of its operating environment.

With reference to FIGS. 6 to 10, there is illustrated an apparatus 200 in accordance with another embodiment of the present invention. As shown, the apparatus 200 includes a housing 220 which has an air-inlet 222 and an air-outlet 224. The apparatus 200 has a fan 226 arranged to drive the air passing from the air-inlet 222, and through a diffusing member 232 disposed within the chamber between the air-inlet 222 and the air-outlet 224 so as to mix the air with diffused substance and further expel to the surrounding via the air-outlet 224.

In this embodiment, the apparatus 200 also includes a container 230 in the lower part of the apparatus 200 with a conduit 234 extending to an opening 236, configured as a push button on the housing, so as to provide an accessible opening to refill the container with chemical substance. The apparatus is supported by a base 240 placed under the container 230. A power port 260 is arranged adjacent to the base 240 for connecting to an external power source. The power port can also be arranged anywhere else on the apparatus 200.

Figure 8:
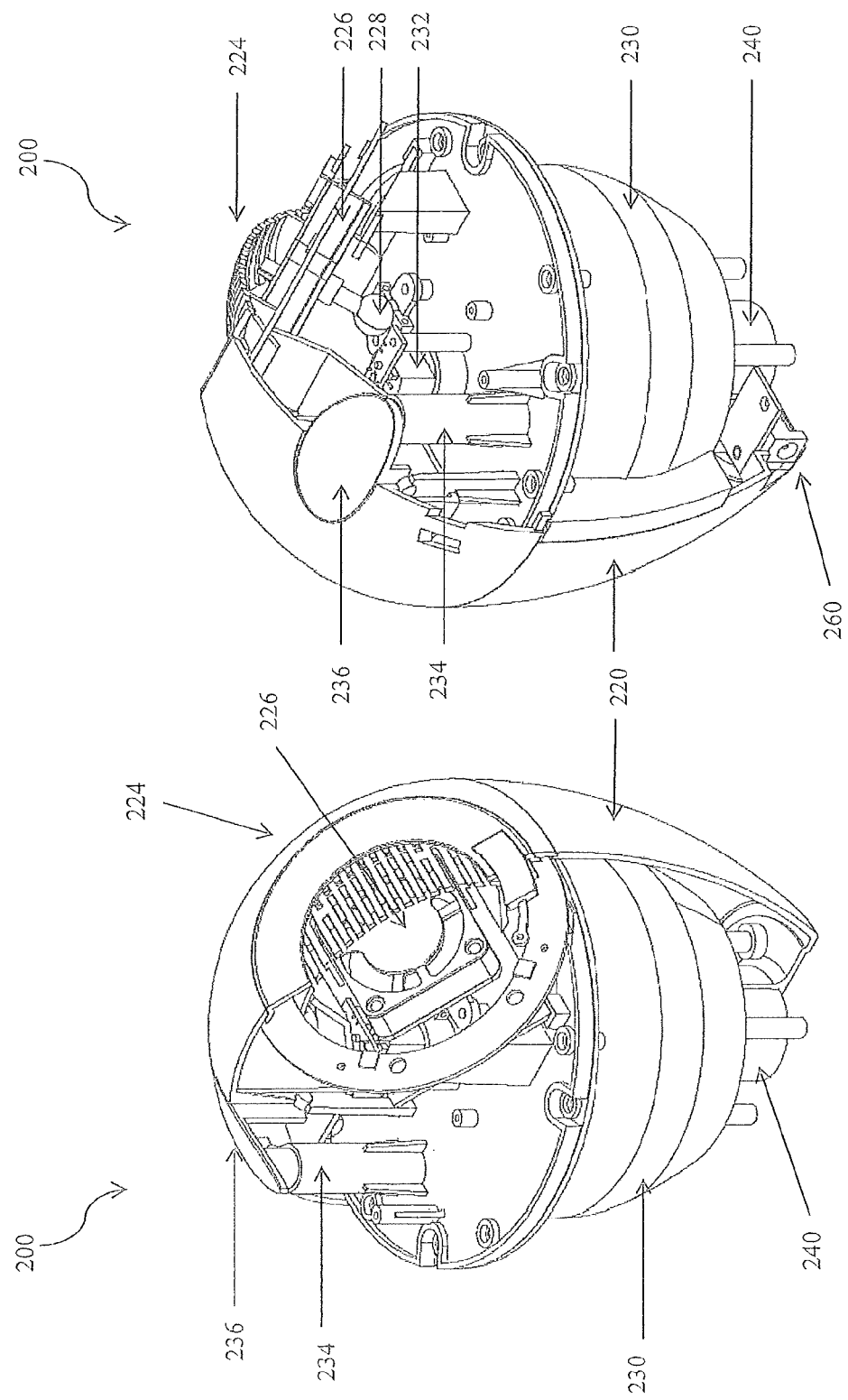
FIG. 8 is a front and rear cut away view of the apparatus of FIG. 6.
Figure 9:
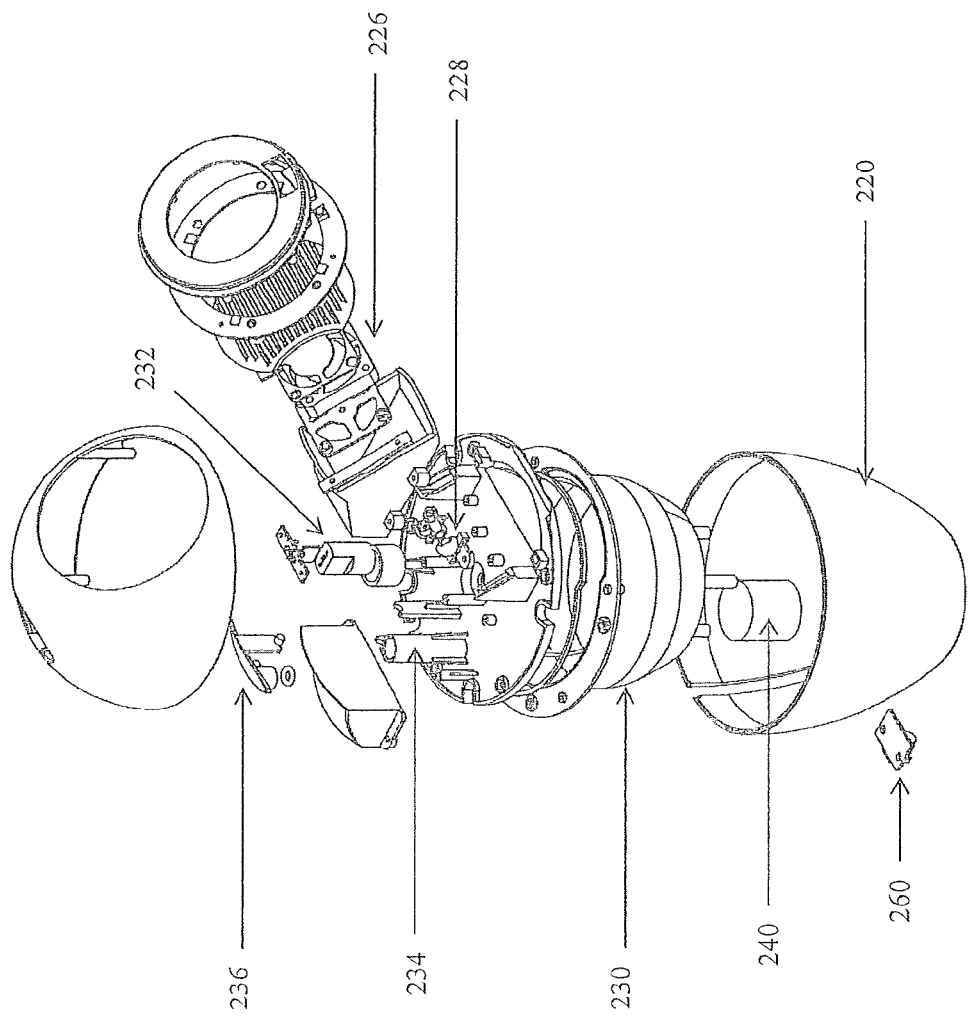
FIG. 9 is an exploded view of the apparatus of FIG. 6.
Figure 10:
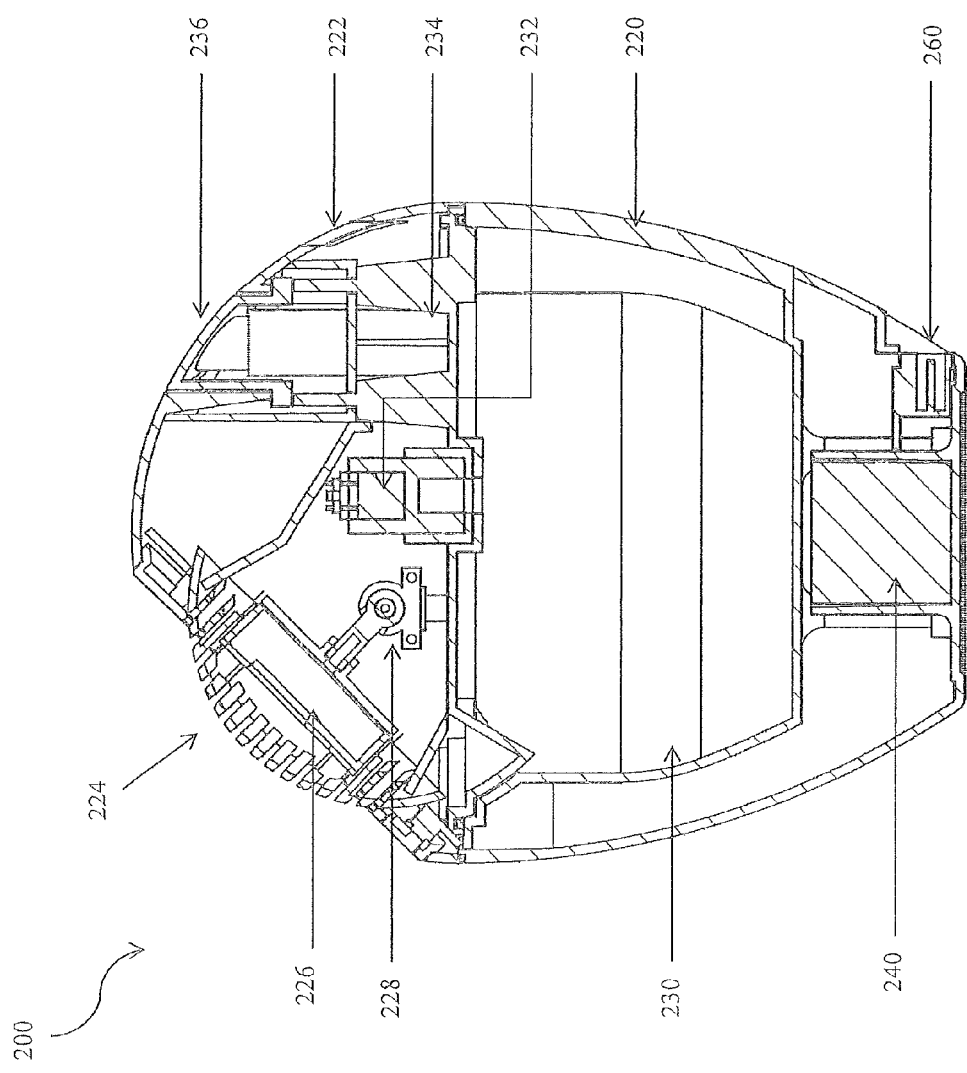
FIG. 10 is a cut away side view of the apparatus of FIG. 6.

As shown in FIGS. 8 to 10, the fan 226 is connected with a rotatable ball bearing component 228 so as to provide a movable joint to engage the fan with the apparatus. Accordingly, in this example, the fan 226 is movable and thus the direction of the air flowing from the apparatus 200 is adjustable. This is advantageous as the adjustable fan allows for a better distribution of scented air which exits the air-outlet 224 to the surrounding atmosphere.

In this embodiment, the air-inlet 222 is positioned directly behind the air-outlet 224, and the diffusing member 232 is arranged within the chamber and disposed between the air-inlet 222 and the air-outlet 224. With this arrangement, the air driven by the fan 226 can flow directly from the air-inlet 222, pass through the diffusing member 232 and exit via the air-outlet 224. This is advantageous in that the arrangement enables a larger portion of the air to pass through the diffusing member 232 so as to allow a better diffusion of chemical substance into the air before exiting via the air-outlet 224.

Preferably, the opening 226 of the container 230 is configured as a push button on the housing 220. The opening 226 comprises a spring 238 such that when pushing down the button, it opens the conduit 234 for refiling the chemical substance into the container 230. This is advantageous in that the arrangement minimizes the force required to open the conduit and is easy to operate.

Figure 11:
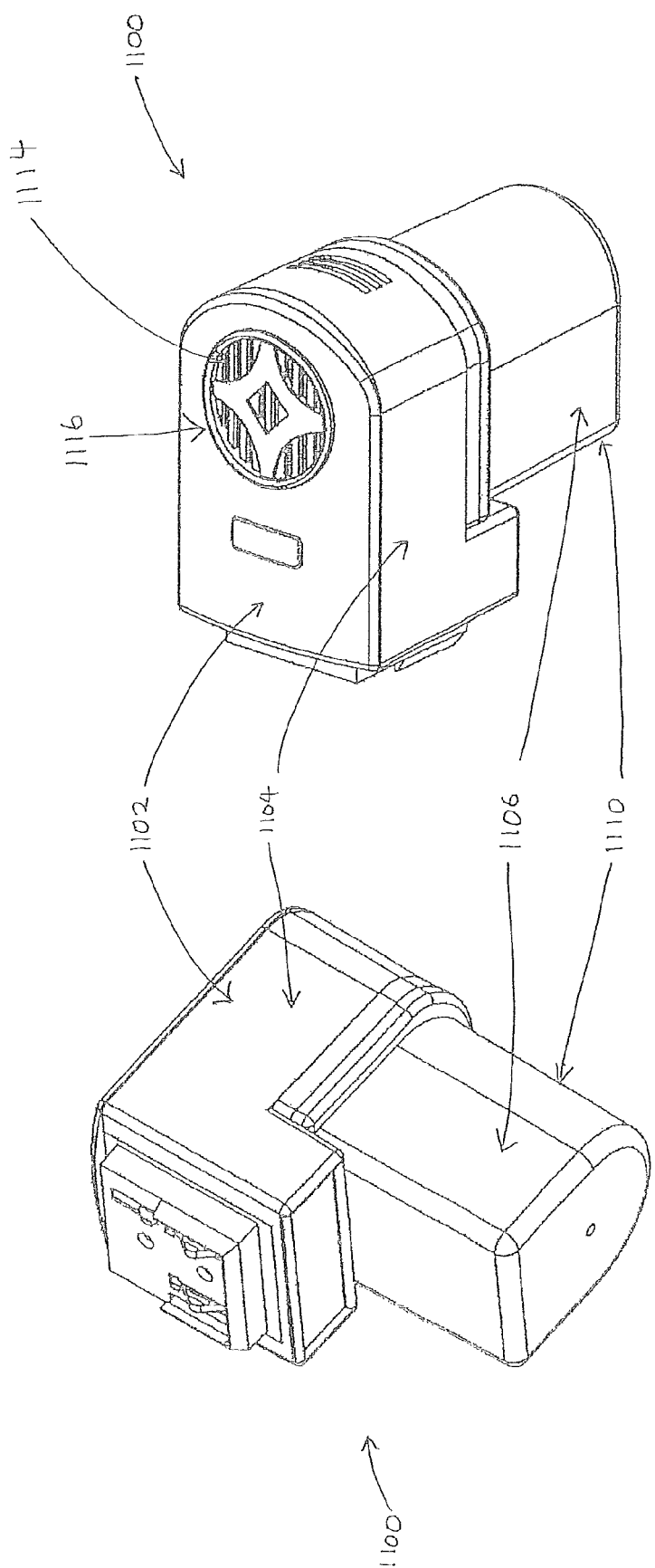
FIG. 11 is a top and rear perspective view of an apparatus for diffusing a chemical substance in accordance with another embodiment of the present invention.
Figure 12:
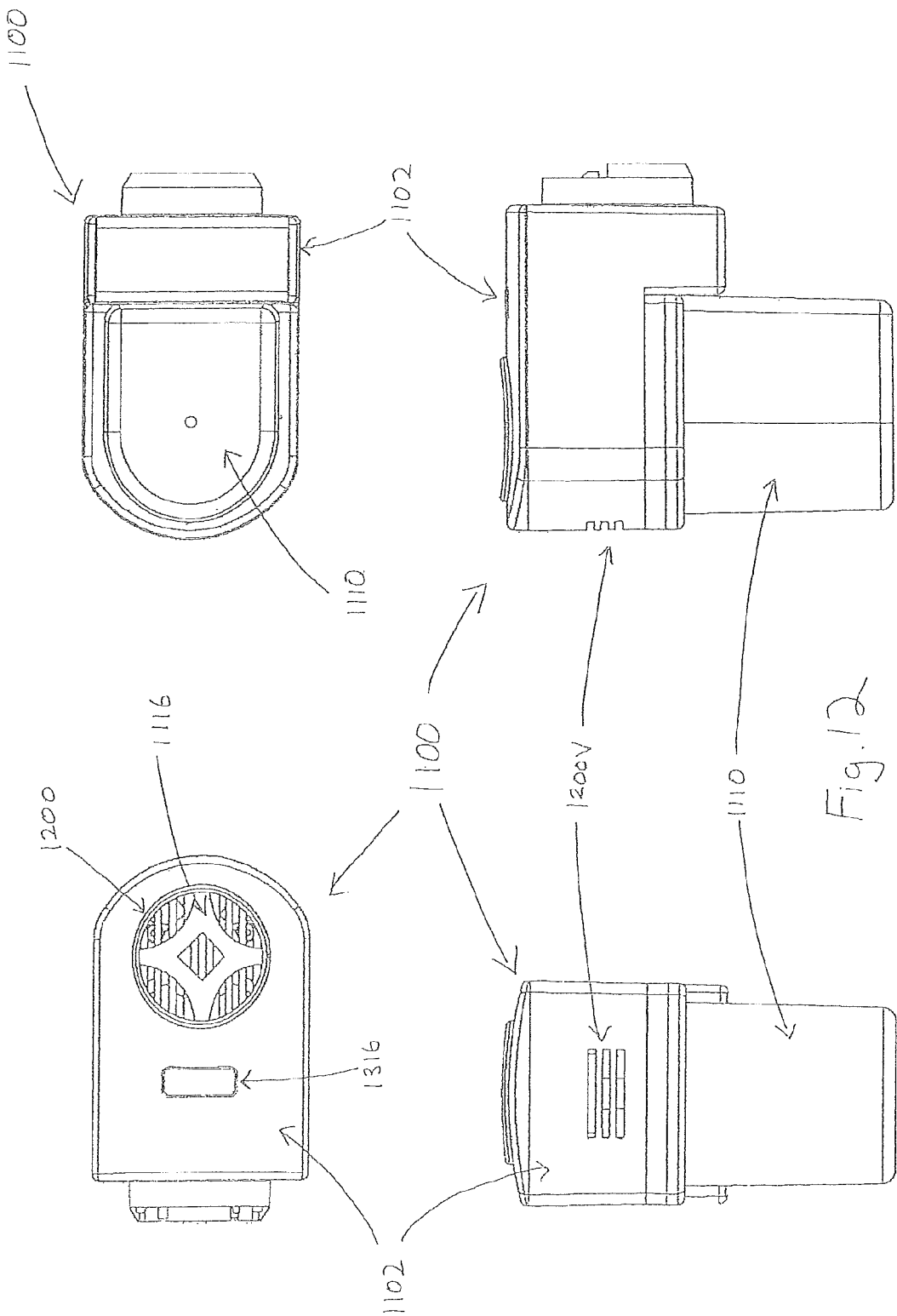
FIG. 12 is a top, side, bottom and front view of the apparatus for diffusing a chemical substance in accordance with FIG. 11.
Figure 13:
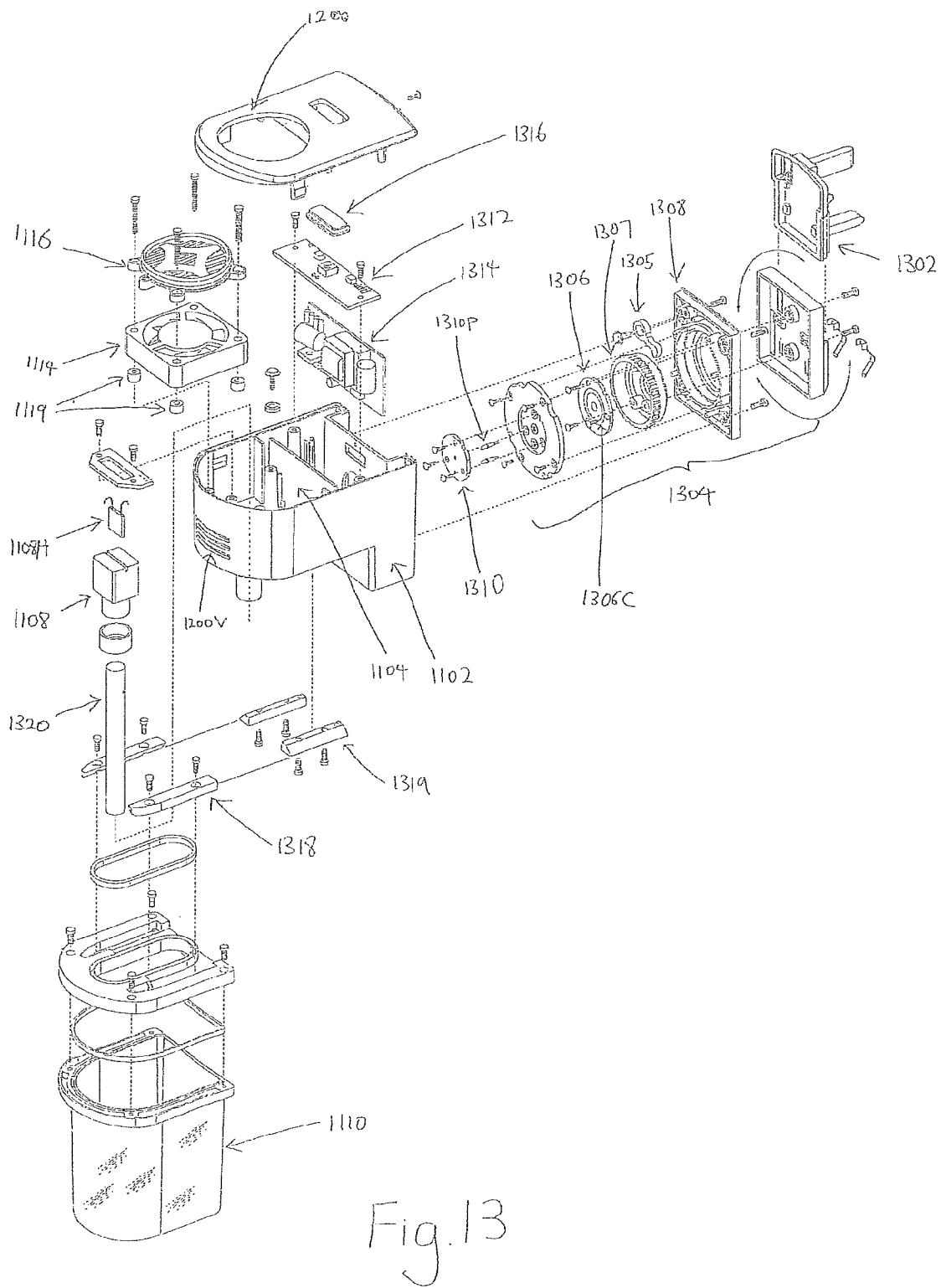
FIG. 13 is an exploded perspective view of the apparatus for diffusing a chemical substance of FIG. 11

With reference to FIGS. 11, 12 and 13 there is illustrated another alternative embodiment of an apparatus for diffusing a chemical substance comprising a chamber having a diffusing member arranged to diffuse a chemical substance to air disposed within the chamber, wherein the chamber is in communication with an air-inlet arranged to receive air from an exterior of the chamber and an air-outlet arranged to expel air from within the chamber.

In this alternative embodiment, the apparatus for diffusing a chemical substance 1100 includes a housing 1102 arranged to form a chamber 1104 in which a chemical substance 1106 can be diffused to the air within the chamber 1104. Once the chemical substance 1106 is diffused to the air within the chamber 1104, the air is then expelled from the chamber 1104 and into the surrounding atmosphere around the apparatus 1100. As mentioned in some of the previous embodiments of the diffusing apparatus, the chemical substance 1106 which is diffused by the apparatus 1102 may be an aromatherapy compound, perfume, scented substances, disinfectant or any other suitable chemical substance which can be diffused into an air and then distributed into a particular area or space.

In this example the housing 1102 includes a diffusing member 1108 arranged to operate within the chamber 1104 formed within the housing 1102. The diffusing member 1108 is arranged to diffuse the chemical substance 1106 by vapouring the chemical substance 1106 stored within a chemical container 1110. The diffusing member 1108 preferably is an electronically heated ceramic stone and is connected to a reservoir or tank 1110 via a wick 1112 which will allow the chemical substance 1106 to be drawn from the container 1110 and be diffused by the diffusing member 1108.

Preferably, electric current may be provided to the heating element 1108H of the diffusing member 1108 so as to evaporate the chemical substance 1106 for diffusion within the chamber 1104 whilst a fan 1114 driven by an electric motor may be arranged near an outlet 1116 or somewhere within the chamber 1104 so as to draw air from the exterior of the chamber 1104 and into the chamber 1104. The fan 1114, in turn, also expels the air from within the chamber 1104 after the air has been mixed with the chemical substance 1106 that has been diffused within the chamber 1104. The resulting effect of this apparatus 1110 is that a chemical substance 1106 stored within the reservoir or container 1110 can be distributed around a room area or space by the fan.

In this specific embodiment, the apparatus 1100 is arranged to be directly connected into a power source such as a mains power socket via a removable electric plug member 1302. This removable electric plug member is not shown in FIGS. 11 and 12 but it is shown in FIG. 13. The removable electric plug member 1302 allows this example embodiment of the apparatus 1110 to be directly plugged into a wall socket without the necessity of using any additional power supply, transformers or cables. This example is advantageous in that in areas where there is limited space, such as in toilets or storage areas where it will generally be inconvenient to have a larger unit, the apparatus can simply be inserted into a power socket so as to diffuse a chemical substance 1106.

Preferably, the electric plug member 1302 can be removably engaged to the apparatus 1100 via a sliding slot arrangement as shown in this example embodiment. By allowing the electric plug member 1302 to be removably engaged, various plugs for different socket arrangements of different countries can be used by simply removing and replacing the electrical plug member with an alternative plug suitable for other jurisdictions. This is advantageous in that a single apparatus 1100 unit can operate within multiple jurisdictions where the mains power socket may be different by simply changing the removable plug member 1302 to suit the mains power socket of the particular country.

In this embodiment, it may be preferable that the unit 1100 is constantly stored, operated and used in an upright position, that is with the chemical container 1110 substantially point towards the bottom of the apparatus 1100. This is because the container 1110 may store a chemical substance 1106 in liquid form. As such the unit in operation cannot be inserted into a mains power socket upside down as the chemical substances 1106 within the container 1110 may leak from the container 1110 and into the housing 1102. In turn, this may cause a substantial portion of the chemical substance 1106 to leak through the chamber 1104 and become wasted or lost.

As shown in this example, in order to ensure that the apparatus 1100 is able to operate the right way up, the electric plug member is arranged to be connected to a rotatable power conduit 1304 that allows electrical energy from a power source, such as the mains power socket, to be delivered to the apparatus 1100 even if the electric plug member 1302 is rotated about the apparatus 1110. The mechanism of the rotatable power conduit 1304 may include a rotatable circuit board 1306 which ensures a continuous electrical conductivity even when rotated in any direction. An example of this arrangement is further described with reference to the exploded diagram of FIG. 13.

In this embodiment the rotatable power conduit 1304 allows the apparatus 1100 to rotate about the electrical plug member 1302 such that it can remain the correct way up whilst also ensuring that electrical energy can continuously be delivered to the apparatus 1100 irrespective of the angle in which the apparatus 1100 is rotated about the electrical plug member 1302. This is particularly advantageous in certain situations where there is no commonality in whether a power socket is installed in any particular orientation and thus allows an end user to rotate the apparatus 1100 into a correct position so as to avoid the chemical substances 1106 stored within the container 1110 to leak from the apparatus 1100.

With reference to FIG. 13 there is illustrated an exploded perspective view of an apparatus of FIGS. 11 and 12. In this embodiment, the electrical plug member 1302 is connected to the apparatus 1110 via a rotatable power conduit arrangement 1304 which includes a support board 1308 having a rotating shaft that provides a shaft for the plug member 1302 to rotate about and a rotating circuit board 1306 which has a circular conductive track 1306C. By including a circular conductive track 1306C, the circuit arrangement can be rotated 360 degrees in any direction whilst continuously remaining in electrical connection with a stationary electrical conduit board 1310 attached to the housing 1102. As shown in this example, the stationary electric conduit board 1310 includes two resilient-electrically connected pins 1310P which resiliently abut the circular conductive track 1306C of the rotating circuit board 1306 (and/or the axis of the rotating circuit board) so that electrical energy can be continuously transmitted from the plug member 1302 to the apparatus 1100 itself when the plug member 1302 is rotated.

As shown in the example shown in FIG. 13, the plug member 1302 is electrically connected to a disc-shaped rotating circuit board 1306 by an electric cable (not shown) such that when the electric plug member is rotated about the axis defined by a support board 1308 the disc-shaped circuit board 1308 is also rotated with the plug member 1302. The disc-shaped rotatable circuit board 1306 may include one or more annular conductive tracks 1306C which maintain a constant electrical connection with the resilient pins 1310P. As the plug member 1302 is in constant electrical connection with the resilient pins 1310P which are in turn engaged to a stationary printed circuit board 1310, electrical energy can then be transmitted from the plug member 1302 to the disc-shaped stationary wiring board 1310. In turn, the control circuits 1312 via a power transformer 1314 can be energized.

Once the control circuit 1312 and transformer 1314 are energized, electrical power at a suitable voltage can then be supplied to the fan unit 1114 and the heating elements 1108H so as to diffuse the chemical substance stored in the container 1110. The control circuits 1312 may also be energized to provide processing and controlling. functions, for example, to control the speed of the fan 1114 or heat of the heating element 1108H in the diffusing member 1108, or to respond to user's input, such as to turn on/off via a switch 1316 or to operate on a timer or a desired operation speed or temperature.

In this embodiment the container is arranged to store a chemical substance to be diffused and is arranged to be slidably engaged and disengaged to the apparatus 1110 through slidable members 1318 and 1319 into a housing 1102. In this example, the housing 1102 has a catalytic burner within a chamber 1104 to operate as a diffusing member 1108. The catalytic burner may also have metallic substances, such as platinum arranged to be within a ceramic matrix such that when it is heated by an electric heating element 1108H, the heat is evenly distributed through-out the ceramic matrix whilst a catalytic function provided by the metallic substances may also assist in the vaporization of the chemical substance.

Preferably, the chemical substances within the container 1110 can be drawn by a wick 1320 connected to the diffusing member 1108 through capillary action and subsequently diffused within the chamber formed by the housing 1102. In turn, vents 1200V and openings 1200 within the housing allow air to be drawn in by a fan 1114 such that it can be expelled from the housing through a grill cover 1116.

Also shown in this embodiment, the fan 1114 may also be secured within the chamber via cushioned O-rings 1119 which assist in reducing the vibrations from the rotation of the fan 1114. This is advantageous in that this arrangement will reduce the noise and vibrations generated during the usage of the device.

Also shown in this example embodiment is that the rotatable power conduit 1304 includes a rotational gear 1307 which interacts with the detent 28 that fits into the teeth of the gear 1307. The detent 1305 may be spring loaded so as to improve its interaction with the teeth of the gear. By including such an arrangement, the detent 1305 is able to limit the rotation movement of the electric plug member 1302 such that when the rotatable power conduit 1304 is rotated, a user may be able to rotate the apparatus 1100 into a specific angle desired.

This alternative embodiment is advantageous in that it provides a wall mounted apparatus 1100 for diffusing a chemical substance and thus minimize the requirements for additional electrical cables or transformers that take up additional space. In addition, this particular embodiment of the apparatus 1100 includes a rotatable power conduit 1304 such that different configurations of electrical sockets can be used to ensure that the device remains the correct way up during operation.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The present invention provides an apparatus for diffusing a chemical substance comprising: a chamber having a diffusing member arranged to diffuse a chemical substance to air disposed within the chamber, wherein the chamber is in communication with an air-inlet arranged to receive air from an exterior of the chamber and an air-outlet arranged to expel air from within the chamber.

The invention claimed is:

1. An apparatus for diffusing a chemical substance comprising:
    a chamber having a diffusing member arranged to diffuse a chemical substance to air disposed within the chamber,
    wherein the chamber is in communication with an air-inlet arranged to receive air from an exterior of the chamber and an air-outlet arranged to expel air from within the chamber,
    wherein the diffusing member is a catalytic burner having a ceramic matrix, the ceramic matrix arranged to be heated by an electric heating element.

2. An apparatus in accordance with claim 1, wherein the chamber is defined by a housing arranged to surround the diffusing member.

3. An apparatus in accordance with claim 1, further comprising a fan arranged to drive air from the air-inlet and through the chamber to be expelled through the air-outlet.

4. An apparatus in accordance with claim 2, wherein the diffusing member is in liquid communication with a container arranged to contain the chemical substance.

5. An apparatus in accordance with claim 2, further including a power conduit arranged to deliver electrical power to the apparatus from a power source, wherein the power conduit is rotatable relative to the housing.

6. An apparatus in accordance with claim 5, wherein the power conduit includes a removable electrical plug member arranged to be connected to the power source.

7. An apparatus in accordance with claim 5, wherein the power conduit includes a rotatable circuit member arranged to form a continuous electrical connection between the power conduit and the apparatus as the power conduit is rotated relative to the housing.

8. An apparatus in accordance with claim 7, wherein the rotatable circuit member is a printed circuit board having a circular conductive track arranged to form the continuous electrical connection between the power conduit and the apparatus as the power conduit is rotated relative to the housing.

9. An apparatus in accordance with claim 1 wherein the catalytic burner is heated to a temperature of between 50 to 80 degrees Celsius.

10. An apparatus in accordance with claim 7, wherein the power conduit includes a detent arranged to restrict the rotation of the power conduit about the housing.

11. An apparatus in accordance with claim 5, wherein the power source is a mains power supply socket.

12. An apparatus in accordance with claim 3, wherein the fan is controlled by a controller to vary the speed of the fan.

13. An apparatus in accordance with claim 1, wherein the chemical substance is an aromatherapy compound.

14. An apparatus in accordance with claim 4, wherein the container is arranged to slidably engage or disengage with the housing.

* * * * *